May 2, 1933. M. DENOYEL Plant Pat. 62
ROSE
Filed July 7, 1932
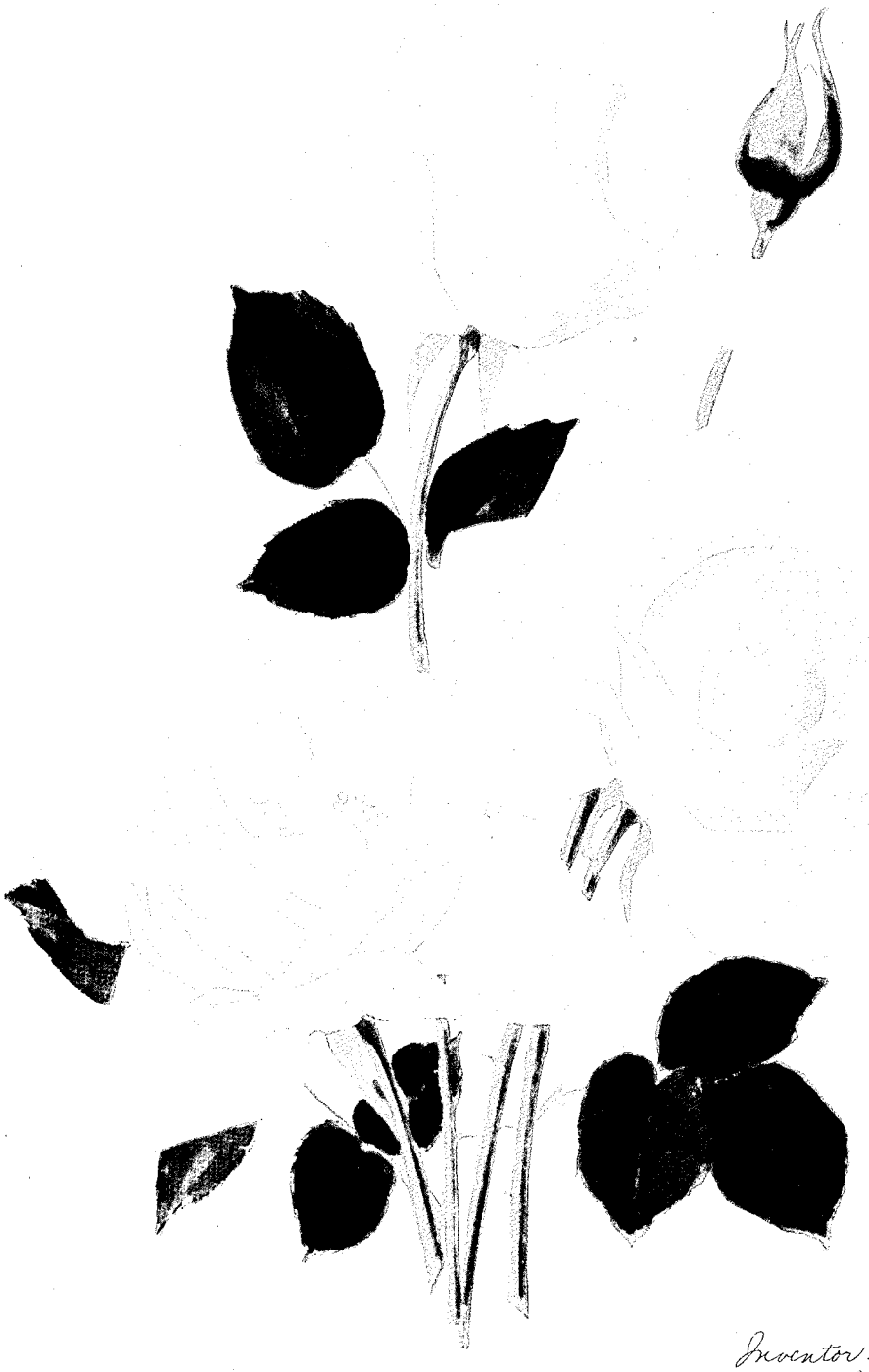
Inventor:
Marguerite Denoyel
by: Robb & Robb
Attorneys Patented May 2, 1933

Plant Pat. 62

UNITED STATES PATENT OFFICE

MARGUERITE DÉNOYEL, OF VENISSIEUX NEAR LYON, FRANCE, ASSIGNOR TO JACKSON & PERKINS COMPANY, OF NEWARK, NEW YORK

ROSE

Application filed July 7, 1932. Serial No. 621,280.

This invention or discovery relates to a new and distinct variety of rose, produced by repeated cross-breeding for several generations of a Hybrid Perpetual seedling with a Pernetiana seedling.

The object in view was to obtain a variety which possessed the desirable characteristics of the two mentioned strains. It is believed that in this new variety for the first time a Hybrid Perpetual has been successfully and evenly mixed with the Pernetiana so as to conserve the hardiness and robustness of the former, together with the size and form of its bloom, while showing the main characteristics of continuous blooming, color combination and glossy foliage obtainable only from the latter strain.

It is also notable that the Pernetiana strain is vividly dominant in the form and shape of the thorns and their unique coloring, green at the base and red at the point.

The bloom of this new variety is extraordinarily large, similar to the old type of Hybrid Perpetual, while the color is new for the hardy class: orange, gold, coral and salmon with a general tonality of brilliant coral suffused with salmon.

To obtain these results, the progeny of the original cross had to be intercrossed for several generations so as to fix the desired characteristics of hardiness, vigor and bloom size of one strain (Hybrid Perpetual) and the foliage, colors and continuity of bloom of the other strain (Pernetiana).

This new rose stands winter severity at a much farther north latitude than any previously known Pernetiana or Hybrid Tea, and it will be desirable in a large territory where Hybrid Teas can be grown only with extreme difficulties.

The following is a brief technical description of the new variety:—

Parentage:—

Seedling.

*Seed parent.*—Unnamed Hybrid Perpetual seedling.

*Pollen parent.*—Unnamed Pernetiana seedling.

Classification:—

Hybrid Perpetual Hybrid.

*Flower*

Blooming habit:—

*Recurrent.*—Continuous.

Bud:—

*Size.*—Very large.

*Form.*—Ovoid. Not affected by wet or hot weather.

*Color.*—When sepals first divide, orange with greenish tint. When petals begin to unfurl, orange. When half blown: inside of petals coral pink, reverse of petals orange salmon.

*Sepals.*—Serrated. Curled back: when bud is half blown.

*Calyx.*—Funnel shape. Large, smooth. Russet apple odor when rubbed.

*Peduncle.*—Long, prickly, light green, heavy.

*Opening.*—Opens well—is not affected by adverse conditions.

Bloom:—

*Size.*—Very large. When fully expanded 4 to 4½″.

*Borne.*—Singly.

*Stems.*—Long, strong.

*Form.*—When first open, high center, globular.

*Permanence.*—Retains its form to the end.

*Petalage.*—Very double.

*Color.*—Center of flower, coral. Outer petals, salmon orange. Base of petals (aiglet) yellow. Inside of petals, satiny coral. Reverse of petals, orange carmine. General tonality from a distance, salmon coral.

*Discoloration.*—Tonality at end of first day, coral. Second day, coral. Third day, salmon pink.

Petals:—

*Texture.*—Thick. Not affected by hot or wet weather.

*Appearance.*—Inside, satiny: outside, shiny.

*Form.*—Round.

*Arrangement.*—Imbricated. Petaloids in center; few, large.

*Persistence.*—Drop off cleanly.

*Fragrance.*—Moderate.

*Nature.*—Fruity.

*Lastingness.*—On the plant—very long. As cut flower—very long.

Genital organs:—

*Stamens, anthers.*—Large, many. Color—white. Arrangement—regular around styles.

*Stamens, filaments (threads).*—Medium. Color—white.

*Pollen.*—Lemon yellow.

*Styles.*—Loosely separated, uneven length. Medium, heavy.

*Stigmas.*—White.

*Ovaries.*—All enclosed in calyx.

Fruit:—

Variety is fertile with its own pollen.

*Form.*—Round.

*Aspect.*—Smooth.

*Color at maturity.*—Yellow.

*Sepals.*—Caducous; recurved.

*Plant*

Form:—

Bush.

Growth:—

Vigorous; branching.

Foliage:—

Five leaflets.

*Size.*—Medium.

*Quantity.*—Sparse.

*Color.*—New foliage: Upper side—dark green; bronzy. Under side—light green. Old foliage: Upper side—dark green. Under side—light reddish green.

*Shape.*—Oval pointed.

*Texture.*—Upper side—leathery, glossy. Under side—rough. Ribs and veins—ordinary.

*Edge.*—Serrated.

*Serration.*—Single; small.

*Leaf stem.*—Green. Under side—prickles.

*Stipules.*—Medium. Smooth.

*Disease Resistance.*—Resistant.

Wood:—

*New wood.*—Color—light green. Bark—smooth.

*Oldwood.*—Color—green. Bark—smooth.

Thorns:—

*Quantity.*—On main stalks from base—many. On laterals from stalk—few.

*Form.*—Broad base; long; straight.

*Color when young.*—Green and red.

*Position.*—Irregular.

*Prickles.*—Quantity: On main stalks—few. On laterals—few. Color—green.

*Short needles.*—Quantity: On main stalks—none. On laterals—none.

I claim:—

The new variety of rose, characterized by the hardiness and robustness of the Hybrid Perpetual, the size and form of bloom, combined with the continuous blooming, color combination and glossy foliage of the Pernetiana strain, as shown and described.

In testimony whereof I affix my signature.

MARGUERITE DÉNOYEL.